United States Patent
Gordon et al.

(10) Patent No.: US 12,201,078 B2
(45) Date of Patent: Jan. 21, 2025

(54) HEMP CULTIVAR NAMED 'CBDRX18'

(71) Applicant: FUNCTIONAL REMEDIES INTERNATIONAL LLC, Superior, CO (US)

(72) Inventors: Timothy A. Gordon, Loveland, CO (US); Ari T. Helland, Pueblo, CO (US)

(73) Assignee: FRTJC, LLC, Alexandria, VA (US)

( * ) Notice: Subject to any disclaimer, the term of this patent is extended or adjusted under 35 U.S.C. 154(b) by 355 days.

(21) Appl. No.: 17/210,947

(22) Filed: Mar. 24, 2021

(65) Prior Publication Data

US 2021/0352864 A1    Nov. 18, 2021

Related U.S. Application Data

(60) Provisional application No. 63/023,344, filed on May 12, 2020.

(51) Int. Cl.
*A01H 6/28* (2018.01)
*A01H 5/10* (2018.01)
*A01H 5/12* (2018.01)
*C12N 5/04* (2006.01)

(52) U.S. Cl.
CPC .............. *A01H 6/28* (2018.05); *A01H 5/10* (2013.01); *A01H 5/12* (2013.01); *C12N 5/04* (2013.01)

(58) Field of Classification Search
CPC ........................................................ A01H 6/28
See application file for complete search history.

(56) References Cited

PUBLICATIONS

Barcaccia et al, Frontiers in Plant Science (2020) 11:1-19.*
Grassa et al, BioRxiv, Dec. 11, 2018, pp. 1-31.*
Grassa et al., A complete Cannabis chromosome assembly and adaptive admixture for elevated cannabidiol (CBD) content; BioRxiv, pp. 1-31 (Dec. 11, 2018).
NCBI Cannabis sativa annotation release, CS10 (CBDRx18) assembly accession (https://www.ncbi.nlm.nih.gov/assembly/GCF_900626175.1/).

* cited by examiner

*Primary Examiner* — Mykola V. Kovalenko
(74) *Attorney, Agent, or Firm* — Weatherly IP Solutions, LLC; James M. Weatherly

(57) ABSTRACT

One embodiment relates to the plants, seeds and tissue cultures of hemp cultivar 'CBDRx18', and to methods for producing a hemp plant produced by crossing such plants with themselves, with another hemp plant, such as a plant of another genotype, or with vegetatively propagating said plant. Another embodiment further relates to seeds and plants produced by such crossing. Further embodiments relate to parts of such plants, and products produced.

17 Claims, No Drawings

HEMP CULTIVAR NAMED 'CBDRX18'

CROSS REFERENCE TO RELATED APPLICATIONS

The present application claims priority to U.S. Provisional Application No. 63/023,344, as filed on May 12, 2020, the entire contents of which are herein incorporated by reference for all that are taught and disclosed.

BACKGROUND

Background

All publications cited in this application are herein incorporated by reference.

Industrial hemp in the United States is cannabis which contains 0.3% or less total sample dry weight of Δ9-Tetrahydrocannabinal (THC). In contemporary varieties of cannabis, THC content is normally above the 0.30% threshold. THC is one of an estimated 85 cannabinoids (a class of terpenoids) synthesized in Cannabis species (El-Alfy et al., 2010, "Antidepressant-like effect of delta-9-tetrahydrocannabinol and other cannabinoids isolated from Cannabis sativa L", Pharmacology Biochemistry and Behavior 95 (4): 434-42).

The foregoing examples of the related art and limitations related therewith are intended to be illustrative and not exclusive. Other limitations of the related art will become apparent to those of skill in the art upon a reading of the specification.

SUMMARY

It is to be understood that the embodiments include a variety of different versions or embodiments, and this Summary is not meant to be limiting or all-inclusive. This Summary provides some general descriptions of some of the embodiments, but may also include some more specific descriptions of other embodiments.

An embodiment provides an industrial hemp cultivar designated 'CBDRx18'. Another embodiment relates to the seeds and tissue cultures of hemp cultivar 'CBDRx18' as well as the plants produced form the seeds and tissue cultures, to the plants of hemp cultivar 'CBDRx18', and to methods for producing a cannabis plant by crossing hemp cultivar 'CBDRx18' with itself or another cannabis plant, and the creation of variants by mutagenesis or transformation of hemp cultivar 'CBDRx18'.

Any such methods using hemp cultivar 'CBDRx18' are a further embodiment: selfing, backcrosses, hybrid production, crosses to populations, and the like. All plants produced using hemp cultivar 'CBDRx18' as at least one parent are within the scope of the embodiments. Advantageously, hemp cultivar 'CBDRx18' could be used in crosses with other, different plants to produce first generation ($F_1$) hybrid seeds and plants with superior characteristics.

Another embodiment provides for single or multiple gene converted plants of hemp cultivar 'CBDRx18'. The transferred gene(s) may be a dominant or recessive allele. The transferred gene(s) may confer such traits as herbicide tolerance, insect tolerance, tolerance for bacterial, fungal, or viral disease, male fertility, male sterility, enhanced nutritional quality, environmental stress tolerance, modified yield, modified oil content, and modified industrial usage. The gene may be naturally occurring or a transgene introduced through genetic engineering techniques.

Another embodiment provides for regenerable cells for use in tissue culture of hemp cultivar 'CBDRx18'. The tissue culture may be capable of regenerating plants having all the physiological and morphological characteristics of the foregoing hemp plant, and of regenerating plants having substantially the same genotype as the foregoing hemp plant. The regenerable cells in such tissue cultures may be embryos, protoplasts, meristematic cells, callus, pollen, leaves, ovules, anthers, cotyledons, hypocotyl, pistils, roots, root tips, flowers, seeds, plant, petiole, or stems. Still a further embodiment provides for hemp plants regenerated from the tissue cultures of hemp cultivar 'CBDRx18'.

Another embodiment relates to a method of vegetatively propagating hemp cultivar 'CBDRx18' comprising the steps of: (a) collecting tissue capable of being propagated from the plant; (b) cultivating said tissue to obtain proliferated shoots; and (c) rooting said proliferated shoots to obtain rooted plantlets.

Another embodiment provides for a method for producing a seed of a hemp plant derived from hemp cultivar 'CBDRx18' comprising the steps of: (a) crossing the hemp plant with itself or a second hemp plant, and (b) allowing seed of a 'CBDRx18'-derived hemp plant to form.

Further embodiments provide for a method of producing a commodity plant product from hemp cultivar 'CBDRx18'.

Various embodiments are set forth in the Detailed Description as provided herein and as embodied by the claims. It should be understood, however, that this Summary does not contain all of the aspects and embodiments, is not meant to be limiting or restrictive in any manner, and that embodiment(s) as disclosed herein is/are understood by those of ordinary skill in the art to encompass obvious improvements and modifications thereto.

In addition to the exemplary aspects and embodiments described above, further aspects and embodiments will become apparent by study of the following descriptions.

DETAILED DESCRIPTION

The embodiments recited herein relates to a novel and distinct hemp (Cannabis sativa) cultivar designated 'CBDRx18', and to the seeds, plants, plant parts, and tissue culture produced by that hemp cultivar. The embodiments further relate to products produced from hemp cultivar 'CBDRx18', including, but not limited to, cannabinoids.

Hemp cultivar 'CBDRx18' has shown uniformity and stability, as described in the following variety description information. Hemp cultivar 'CBDRx18' was tested for uniformity and stability a sufficient number of generations with careful attention to uniformity of plant type and has been increased with continued observation for uniformity.

Hemp cultivar 'CBDRx18' has the following morphologic and other characteristics based primarily on data collected in Pueblo, Colorado on 6 to 9-month-old plants.

Classification:
    Family: Cannabaceae
    Species: *Cannabis sativa* L.
    Denomination: 'CBDRx18'
    Propagation: Vegetative cuttings
    Time to produce a rooted young plant: 28 days
Plant Description:
    Height: 101 cm to 110 cm
    Diameter: 91 cm to 110 cm
    Branching: Nodal axillary
    Time to flower: 85 to 100 days
    Growth: Very vigorous annual Stem:
    Length: 19 cm to 25 cm
    Width: 0.3 cm to 0.7 cm
    Color: Green to pigment green
    Texture: Woody/soft stem
    Lateral branch length: 35 cm to 50 cm
    Average number of nodes: 6 to 8
    Average internode length: 12 cm to 14 cm
Leaves:
    Type/Form: Compound
    Arrangement: Nodal
    Leaf width: 16 cm to 19 cm
    Leaf length: 22 cm to 27 cm
    Number of leaflets per leaf: 5 to 9
    Leaflet shape: Digitate
    Leaflet length: 20 cm to 27 cm
    Leaflet width: 1 cm to 4 cm
    Leaflet margin: 1 cm to 4 cm
    Leaflet apex: 0.2 cm
    Leaflet base: 0.7 cm to 1.0 cm
    Leaflet color, upper surface: Green
    Leaflet color, lower surface: Green
    Venation pattern, upper and lower leaflet surfaces: Pinnate
    Texture (both surfaces): Rough
    Fragrance: Fruit-floral
    Stipules: 1.0 cm
Petioles:
    Length: 6.0 cm
    Diameter: 0.3 cm
Inflorescence:
    Appearance and arrangement: Flowers mostly regular, staminate in racemes, pistillate in dense clusters or spikes
    Fragrance: Floral
    Time to flower: 65 days
    Time of flowering: 37 days
Seed: Absent The oil composition of hemp cultivar 'CBDRx18' is shown in Table 1 below.

TABLE 1

| CBD Oil (flower by dry weight) | Weight Percentage | |
| --- | --- | --- |
| | Third Week of Sexual maturity | Eighth week of sexual maturity |
| Total | 1.6% to 3.4% | 9.6% to 10.3% |

As shown above in Table 1, hemp cultivar 'CBDRx18' has a CBD content in the female flower that ranges between 0.16% and 0.34% by dry weight in the third of sexual maturity and increases to 9.6% to 10.3% at the eighth week of sexual maturity.

Table 2 below shows phytochemical analysis of hemp cultivar 'CBDRx18'. Plants were planted outdoors on May 15, 2020 in Pueblo, Colorado from clones from mother plants that were cut around Apr. 2, 2020. Plants were harvested on Oct. 6, 2020. Harvest included cutting off mostly the tops of plants (leaves) and discarded stem pieces thicker than a pencil. Eight different plants were randomly selected in the fields. The harvested material was dried in a food dehumidifier with hot air, then zip-lock bag shipped the plant material for shipment to the testing facility. A single sample was sent to the testing facility on Oct. 14, 2020.

TABLE 2

| Test | Parameter | Result |
| --- | --- | --- |
| Cannabinoid Profile | CBD | 0.147% |
| | CBDA | 9.78% |
| | CBN | <0.00568% |
| | Delta 9-THC | <0.00568% |
| | THCA | 0.382% |
| | CBC | 0.0132% |
| | CBDVA | 0.0925% |
| | CBG | 0.0253% |
| | CBGA | 0.402% |
| | CBDVA | <0.00568% |
| | Delta 8-THC | <0.0114% |
| | THCV | <0.00568% |
| | CBCA | 0.499% |
| | CBL | <0.00568% |
| | CBNA | <0.00568% |
| | THCVA | <0.00568% |
| | Total THC (THC + (THCA × 0.877)) | 0.336% |
| | Total CBD (CBD + (CBDA × 0.877)) | 8.73% |
| | Total Cannabinoids | 11.3% |
| Terpenes Profile | (−)-alpha-Bisabolol | 2,300 mg/kg |
| | (−)-Isopulegol | <10 mg/kg |
| | (1S)-(+)-3-Carene | <10 mg/kg |
| | (E)-b-Ocimene | <6.0 mg/kg |
| | (R)-(+)-Limonene | 220 mg/kg |
| | (Z)-b-Ocimene | <3.0 mg/kg |
| | alpha-Humulene | 450 mg/kg |
| | alpha-Pinene | 72 mg/kg |
| | alpha-Terpinene | <10 mg/kg |
| | beta-Caryophyllene | 1,800 mg/kg |
| | beta-Myrcene | 1,700 mg/kg |
| | beta-Pinene | 62 mg/kg |
| | Camphene | <10 mg/kg |
| | Eucalyptol | 100 mg/kg |
| | gamma-Terpinene | 11 mg/kg |
| | Linalool | 15 mg/kg |
| | p-Cymene | <10 mg/kg |
| | Terpinolene | <10 mg/kg |

TABLE 2-continued

| Test | Parameter | Result |
|---|---|---|
| Vitamin A | B-carotene | 18,500 IU/100 g |
| | Retinol | <60 IU/100 g |
| | Total Vitamin A | 18,500 IU/100 g |
| Vitamin B12 | Vitamin B12 | <0.440 µg/100 g |
| Vitamin B2 (Riboflavin) | Vitamin B2 (Riboflavin) | 1.07 mg/100 g |
| Vitamin B6 (Pyridoxine) | Vitamin B6 (Pyridoxine) | 1.27 mg/100 g |
| Vitamin C | Vitamin C - Ascorbic Acid | 10.8 mg/100 g |
| Vitamin D | Vitamin D2 | <4 IU/100 g |
| | Vitamin D3 | <4 IU/100 g |
| | Total Vitamin D2 and D3 | <4 IU/100 g |
| Vitamin E | Alpha-Tocopherol | 29.6 mg/100 g |
| | Beta-Tocopherol | 0.248 mg/100 g |
| | Gamma-Tocopherol | 3.71 mg/100 g |
| | Delta-Tocopherol | 0.276 mg/100 g |
| | Total-Tocopherol | 33.8 mg/100 g |
| Vitamin K | Vitamin K1 (FL) (Phylloquinone) | 65.6 µg/g |
| | Menaquinone 4 (FL) (MK4, Vitamin K2) | 1.73 µg/g |
| | trans-Menaquinone 7 (FL) (trans-MK7, Vitamin K2) | Not Detected |
| Total Polyphenols | Total Polyphenols | 13.4 mg/g |
| Chlorophyll | Chlorophyll | 1.09 mg/g |
| Minerals Profile | Calcium (Ca) | 31,400 ppm |
| | Copper (Cu) | 19.5 ppm |
| | Iron (Fe) | 891 ppm |
| | Magnesium (Mg) | 7,660 ppm |
| | Manganese (Mn) | 128 ppm |
| | Phosphorus (P) | 6,890 ppm |
| | Potassium (K) | 19,300 ppm |
| | Sodium (Na) | 49.4 ppm |
| | Zinc (Zn) | 70.3 ppm |
| Fatty Acid Profile | C4:0 (Butyric Acid) | <0.02% |
| | C6:0 (Caproic acid) | <0.02% |
| | C8:0 (Caprylic acid) | <0.02% |
| | C10:0 (Capric acid) | <0.02% |
| | C11:0 (Undecanoic acid) | <0.02% |
| | C12:0 (Lauric Acid) | <0.02% |
| | C14:0 (Myristic acid) | 0.06% |
| | C14:1 (Myristoleic acid) | <0.02% |
| | C15:0 (Pentadecanoic acid) | <0.02% |
| | C15:1 (Pentadecenoic acid) | <0.02% |
| | C16:0 (Palmitic Acid) | 0.47% |
| | C16:1 Omega 7 | <0.04% |
| | C16:1 Total (Palmitoleic Acid + isomers) | 0.06% |
| | C16:2 (Hexadecadienoic Acid) | <0.02% |
| | C16:3 (Hexadecatrienoic Acid) | <0.02% |
| | C16:4 (Hexadecatetraenoic Acid) | <0.02% |
| | C17:0 (Margaric Acid) | <0.02% |
| | C17:1 (Heptadecenoic Acid) | <0.02% |
| | C18:0 (Stearic Acid) | 0.07% |
| | C18:1 (Vaccenic acid) | 0.06% |
| | C18:1 Omega 9 (Oleic Acid) | 0.22% |
| | C18:1, Total (Oleic Acid + isomers) | 0.30% |
| | C18:2 Omega 6 (Linoleic Acid) | 0.64% |
| | C18:2, Total (Linoleic Acid + isomers) | 0.71% |
| | C18:3 Omega 3 (Alpha Linolenic Acid) | 0.74% |
| | C18:3 Omega 6 (Gamma Linolenic Acid) | 0.02% |
| | C18:3, Total (Linolenic Acid + isomers) | 0.76% |
| | C18:4 Omega 3 (Octadecatetraenoic Acid) | 0.02% |
| | C18:4 Total (Octadecatetraenoic Acid) | 0.02% |
| | C20:0 (Arachidic Acid) | 0.05% |
| | C20:1 Omega 9 (Gondoic Acid) | <0.02% |
| | C20:1 Total (Gondoic Acid + isomers) | 0.02% |
| | C20:2 Omega 6 | <0.02% |
| | C20:2 Total (Eicosadienoic Acid) | <0.02% |
| | C20:3 Omega 3 | <0.02% |
| | C20:3 Omega 6 | <0.02% |
| | C20:3, Total (Eicosatrienoic Acid) | <0.02% |
| | C20:4 Omega 3 | <0.02% |
| | C20:4 Omega 6 (Arachidonic Acid) | <0.02% |
| | C20:4, Total (Eicosatetraenoic Acid) | <0.02% |
| | C20:5 Omega 3 (Eicosapentaenoic Acid) | <0.02% |
| | C21:5 Omega 3 (Heneicosapentaenoic Acid) | <0.02% |
| | C22:0 (Behenic Acid) | 0.06% |
| | C22:1 Omega 9 (Erucic Acid) | <0.02% |
| | C22:1 Total (Erucic Acid + isomers) | <0.02% |
| | C22:2 Docosadienoic Omega 6 | <0.02% |

TABLE 2-continued

| Test | Parameter | Result |
|---|---|---|
| | C22:3 Docosatrienoic, Omega 3 | <0.02% |
| | C22:4 Docosatetraenoic Omega 6 | <0.02% |
| | C22:5 Docosapentaenoic Omega 3 | <0.02% |
| | C22:5 Docosapentaenoic Omega 6 | <0.02% |
| | C22:5 Total (Docosapentaenoic Acid) | <0.02% |
| | C22:6 Docosahexaenoic Omega 3 | <0.02% |
| | C24:0 (Lignoceric Acid) | 0.04% |
| | C24:1 Omega 9 (Nervonic Acid) | <0.02% |
| | C24:1 Total (Nervonic Acid + isomers) | <0.02% |
| | Total Omega 3 Isomers | 0.78% |
| | Total Omega 5 Isomers | <0.05% |
| | Total Omega 6 Isomers | 0.67% |
| | Total Omega 7 Isomers | 0.08% |
| | Total Omega 9 Isomers | 0.24% |
| | Total Monounsaturated Fatty Acids | 0.37% |
| | Total Polyunsaturated Fatty Acids | 1.47% |
| | Total Saturated Fatty Acids | 0.80% |
| | Total Trans Fatty Acids | 0.07% |
| | Total Fat as Triglycerides | 2.83% |
| | Total Fatty Acids | 2.71% |
| Omega 11 Fatty Acids | C18:1 Omega 11 | <0.02% |
| | C20:1 Omega 11 | <0.02% |
| | C22:1 Omega 11 | <0.02% |
| | Total Omega 11 Isomers | <0.02% |

An embodiment provides an industrial hemp cultivar designated 'CBDRx18'. Another embodiment relates to the seeds of hemp cultivar 'CBDRx18', to the plants of hemp cultivar 'CBDRx18', and to methods for producing a cannabis plant by crossing hemp cultivar 'CBDRx18' with itself or another cannabis plant, and the creation of variants by mutagenesis or transformation of hemp cultivar 'CBDRx18'.

Any such methods using hemp cultivar 'CBDRx18' are a further embodiment: selfing, backcrosses, hybrid production, crosses to populations, and the like. All plants produced using hemp cultivar 'CBDRx18' as at least one parent are within the scope of the embodiments. Advantageously, hemp cultivar 'CBDRx18' could be used in crosses with other, different plants to produce first generation ($F_1$) hybrid seeds and plants with superior characteristics.

Another embodiment provides for single or multiple gene converted plants of hemp cultivar 'CBDRx18'. The transferred gene(s) may be a dominant or recessive allele. The transferred gene(s) may confer such traits as herbicide tolerance, insect tolerance, tolerance for bacterial, fungal, or viral disease, male fertility, male sterility, enhanced nutritional quality, environmental stress tolerance, modified yield, modified oil content, and modified industrial usage. The gene may be naturally occurring or a transgene introduced through genetic engineering techniques.

Another embodiment provides for regenerable cells for use in tissue culture of hemp cultivar 'CBDRx18'. The tissue culture may be capable of regenerating plants having all the physiological and morphological characteristics of the foregoing hemp plant, and of regenerating plants having substantially the same genotype as the foregoing hemp plant. The regenerable cells in such tissue cultures may be embryos, protoplasts, meristematic cells, callus, pollen, leaves, ovules, anthers, cotyledons, hypocotyl, pistils, roots, root tips, flowers, seeds, plant, petiole, or stems. Still a further embodiment provides for hemp plants regenerated from the tissue cultures of hemp cultivar 'CBDRx18'.

Another embodiment relates to a method of vegetatively propagating hemp cultivar 'CBDRx18' comprising the steps of: (a) collecting tissue capable of being propagated from the plant; (b) cultivating said tissue to obtain proliferated shoots; and (c) rooting said proliferated shoots to obtain rooted plantlets.

Another embodiment provides for a method for producing a seed of a hemp plant derived from hemp cultivar 'CBDRx18' comprising the steps of: (a) crossing the hemp plant with itself or a second hemp plant, and (b) allowing seed of a 'CBDRx18'-derived hemp plant to form.

Further embodiments provide for a method of producing a commodity plant product from hemp cultivar 'CBDRx18'.

Breeding with Hemp Cultivar 'CBDRx18'

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding cultivars are thoroughly tested and compared to appropriate standards in environments representative of the commercial target area(s) for three or more years. The best cultivars are candidates for new commercial varieties; those still deficient in a few traits may be used as parents to produce new populations for further selection.

These processes, which lead to the final step of marketing and distribution, is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. If a single observation is inconclusive, replicated observations provide a better estimate of its genetic worth.

The goal of hemp breeding is to develop new and superior hemp varieties and hybrids. The breeder initially selects and crosses two or more parental cultivars, followed by repeated selfing and selection, producing many new genetic combinations. The breeder can theoretically generate billions of different genetic combinations via crossing, selection, selfing and mutations.

Using Hemp Cultivar 'CBDRx18' to Develop other Hemp Varieties

Hemp varieties such as hemp cultivar 'CBDRx18' are typically developed for industrial usage. However, hemp varieties such as hemp cultivar 'CBDRx18' also provide a source of breeding material that may be used to develop new hemp varieties. Plant breeding techniques known in the art and used in a hemp breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, transformation, and gene editing. These techniques can be used singularly or in combinations. The development of hemp varieties in a breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

One embodiment is directed to methods for producing a hemp plant by crossing a first parent hemp plant with a second parent hemp plant, wherein the first or second hemp plant is the hemp plant from hemp cultivar 'CBDRx18'. Further, both first and second parent hemp plants may be from hemp cultivar 'CBDRx18'. Any plants produced using hemp cultivar 'CBDRx18' as at least one parent are also within the scope of the embodiments. These methods are well known in the art and some of the more commonly used breeding methods are described herein. Descriptions of breeding methods can be found in one of several reference books (e.g., Allard, *Principles of Plant Breeding* (1960); Simmonds, Principles of Crop Improvement (1979); Sneep, et al. (1979); Cooper, S. G., D. S. Douches and E. J. Grafius. 2004.

The following describes breeding methods that may be used with hemp cultivar 'CBDRx18' in the development of further hemp plants. One such embodiment is a method for developing a hemp cultivar 'CBDRx18' progeny plant in a hemp breeding program comprising: obtaining the hemp plant, or a part thereof, of hemp cultivar 'CBDRx18', utilizing said plant, or plant part, as a source of breeding material, and selecting an hemp cultivar 'CBDRx18' progeny plant with molecular markers in common with hemp cultivar 'CBDRx18' and/or with morphological and/or physiological characteristics disclosed herein. Breeding steps that may be used in the hemp plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of hemp cultivar 'CBDRx18' progeny hemp plants, comprising crossing hemp cultivar 'CBDRx18' with another hemp plant, thereby producing a population of hemp plants which derive 50% of their alleles from hemp cultivar 'CBDRx18'. A plant of this population may be selected and repeatedly selfed or sibbed with an hemp cultivar resulting from these successive filial generations. One embodiment is the hemp cultivar produced by this method and that has obtained at least 50% of its alleles from hemp cultivar 'CBDRx18'.

One of ordinary skill in the art of plant breeding would know how to evaluate the traits of two plant varieties to determine if there is no significant difference between the two traits expressed by those varieties. For example, see, Fehr Walt, *Principles of Variety Development*, pp. 261-286 (1987). Thus, embodiments include hemp cultivar 'CBDRx18' progeny hemp plants comprising a combination of at least two hemp cultivar 'CBDRx18' traits disclosed herein, so that said progeny hemp plant is not significantly different for said traits than hemp cultivar 'CBDRx18' as determined at the 5% significance level when grown in the same environmental conditions. Using techniques described herein, molecular markers may be used to identify said progeny plant as a hemp cultivar 'CBDRx18' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease tolerance, pest tolerance, and plant performance in extreme environmental conditions.

Progeny of hemp cultivar 'CBDRx18' may also be characterized through their filial relationship with hemp cultivar 'CBDRx18', as for example, being within a certain number of breeding crosses of hemp cultivar 'CBDRx18'. A breeding cross is a cross made to introduce new genetics into the progeny, and is distinguished from a self or a sib cross, which is made to select among existing genetic alleles. The lower the number of breeding crosses in the pedigree, the closer the relationship between hemp cultivar 'CBDRx18' and its progeny. For example, progeny produced by the methods described herein may be within 1, 2, 3, 4, or 5 breeding crosses of hemp cultivar 'CBDRx18'.

Pedigree Breeding

Pedigree breeding starts with the crossing of two genotypes, such as hemp cultivar 'CBDRx18' and another hemp cultivar having one or more desirable characteristics that is lacking or which complements hemp cultivar 'CBDRx18'. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred cultivar which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

A backcross conversion of hemp cultivar 'CBDRx18' occurs when DNA sequences are introduced through backcrossing, with hemp cultivar 'CBDRx18' utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Frisch M. et al, "Marker-Assisted Backcrossing for Simultaneous Introgression of Two Genes" *Crop Science Society of America*, pp 1716-1725 (2001) and Openshaw, S. J., et al., "Marker-assisted Selection in Backcross Breeding, Proceedings Symposium of the Analysis of Molecular Data" *Crop Science Society of America*, Corvallis, Oreg. (August 1994), where it was demonstrated that a backcross conversion could be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, drought tolerance, nitrogen utilization, industrial enhancements, disease tolerance (bacterial, fungal, or viral), insect tolerance, and herbicide tolerance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into hemp cultivar 'CBDRx18' is at least 1, 2, 3, 4, or 5, and/or no more than 6, 5, 4, 3, or 2. A single locus may contain several transgenes, such as a transgene for disease tolerance that, in the same expression vector, also contains a transgene for herbicide tolerance. The gene for herbicide tolerance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, "Breeding Field Crops" p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in hemp cultivar 'CBDRx18' comprises crossing hemp cultivar 'CBDRx18' plants grown from hemp cultivar 'CBDRx18' seed with plants of another hemp cultivar that comprise the desired trait or locus, selecting $F_1$ progeny plants that comprise the desired trait or locus to produce selected $F_1$ progeny plants, crossing the selected progeny plants with the hemp cultivar 'CBDRx18' plants to produce backcross progeny plants, selecting for backcross progeny plants that have the desired trait or locus and the morphological characteristics of hemp cultivar 'CBDRx18' to produce selected backcross progeny plants, and backcrossing to hemp cultivar 'CBDRx18' three or more times in succession to produce selected fourth or higher backcross progeny plants that comprise said trait or locus. The modified hemp cultivar 'CBDRx18' may be further characterized as having the physiological and morphological characteristics of hemp cultivar 'CBDRx18' listed in Table 1 as determined at the 5% significance level when grown in the same environmental conditions and/or may be characterized by percent similarity or identity to hemp cultivar 'CBDRx18' as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny hemp seed by adding a step at the end of the process that comprises crossing hemp cultivar 'CBDRx18' with the introgressed trait or locus with a different hemp plant and harvesting the resultant first generation progeny hemp seed.

Many single gene traits have been identified that are not regularly selected for in the development of a new variety but that can be improved by backcrossing techniques well-known in the art. Single gene traits may or may not be transgenic. Examples of these traits include, but are not limited to, herbicide tolerance, insect tolerance, tolerance for bacterial, fungal, or viral disease, male fertility, male sterility, modified yield, and modified industrial usage.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, an hemp cultivar may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new hemp varieties.

Therefore, an embodiment of the present disclosure is a method of making a backcross conversion hemp cultivar 'CBDRx18', comprising the steps of crossing a plant of hemp cultivar 'CBDRx18' with a donor plant comprising a desired trait, selecting an $F_1$ progeny plant comprising the desired trait, and backcrossing the selected $F_1$ progeny plant to a plant of hemp cultivar 'CBDRx18' to produce $BC_1$, $BC_2$, $BC_3$, etc. This method may further comprise the step of obtaining a molecular marker profile of hemp cultivar 'CBDRx18' and using the molecular marker profile to select for a progeny plant with the desired trait and the molecular marker profile of hemp cultivar 'CBDRx18'. In one embodiment, the desired trait is a mutant gene, gene, or transgene present in the donor parent.

Recurrent Selection and Mass Selection

Recurrent selection is a method used in a plant breeding program to improve a population of plants. Hemp cultivar 'CBDRx18' is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Mutation Breeding

Mutation breeding is another method of introducing new traits into hemp cultivar 'CBDRx18'. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Variety Development," Macmillan Publishing Company (1993). In addition, mutations created in other hemp plants may be used to produce a backcross conversion of hemp cultivar 'CBDRx18' that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using Agrobacterium-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, see for example Noman, A. et al., "CRISPR-Cas9: Tool for Qualitative and Quantitative Plant Genome Editing" *Frontiers in Plant Science* Vol. 7 November 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476.

Therefore it is another embodiment to use the CRISPR system on hemp cultivar 'CBDRx18' to modify traits and resistances or tolerances to pests, herbicides, and viruses.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing using SAKIMP061. The technique is well known in the art; see for example Malzahn, Aimee et al. "Plant genome editing with TALEN and CRISPR" *Cell & bioscience* vol. 7 21. 24 Apr. 2017.

Therefore, it is another embodiment to use the TALENs system on New Guinea Impatiens variety SAKIMP061 to modify traits and resistances or tolerances to pests, herbicides, and viruses Introduction of a New Trait or Locus into Hemp Cultivar 'CBDRx18'

Hemp cultivar 'CBDRx18' represents a new variety into which a new locus or trait may be introgressed. Direct transformation and backcrossing represent two important methods that can be used to accomplish such an introgression. The term backcross conversion and single locus conversion are used interchangeably to designate the product of a backcrossing program.

Molecular Techniques Using Hemp Cultivar 'CBDRx18'

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to "alter" (the utilization of up-regulation, down-regulation, or gene silencing) the traits of a plant in a specific manner. Any DNA sequences, whether from a different species or from the same species, which are introduced into the genome using transformation or various breeding methods are referred to herein collectively as "transgenes." In some embodiments, a transgenic variant of hemp cultivar 'CBDRx18' may contain at least one transgene. Over the last fifteen to twenty years several methods for producing transgenic plants have been developed, and another embodiment also relates to transgenic variants of the claimed hemp cultivar 'CBDRx18'.

Numerous methods for plant transformation have been developed, including biological and physical plant transformation protocols. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993) and Nakagawa T. et al, "Development of series of gateway binary vectors, pGWBs, for realizing efficient construction of fusion genes for plant transformation" *Journal of Bioscience and Bioengineering* pp 34-41 (2007).

A genetic trait which has been engineered into the genome of a particular hemp plant may then be moved into the genome of another variety using traditional breeding techniques that are well known in the plant breeding arts. For example, a backcrossing approach is commonly used to move a transgene from a transformed hemp cultivar into an already developed hemp cultivar, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Amplified Fragment Length Polymorphisms (AFLPs), Arbitrarily Primed Polymerase Chain Reaction (AP-PCR), DNA Amplification Fingerprinting (DAF), Sequence Characterized Amplified Regions (SCARs), Simple Sequence Repeats (SSRs), and Single Nucleotide Polymorphisms (SNPs) may be used in plant breeding methods utilizing hemp cultivar 'CBDRx18'.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

Hemp is a diploid plant, however the production of double haploids can also be used for the development of plants with a homozygous phenotype in the breeding program. For example, a hemp plant for which hemp cultivar 'CBDRx18' is a parent can be used to produce double haploid plants. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. For example, see, M. Maluszynski et al. (eds), *Doubled Haploid Production in Crop Plants*, (2003).

Thus, an embodiment is a process for making a substantially homozygous hemp cultivar 'CBDRx18' progeny plant by producing or obtaining a seed from the cross of hemp cultivar 'CBDRx18' and another hemp plant and applying double haploid methods to the $F_1$ seed or $F_1$ plant or to any successive filial generation.

In particular, a process of making seed retaining the molecular marker profile of hemp cultivar 'CBDRx18' is contemplated, such process comprising obtaining or producing $F_1$ seed for which hemp cultivar 'CBDRx18' is a parent, inducing doubled haploids to create progeny without the occurrence of meiotic segregation, obtaining the molecular marker profile of hemp cultivar 'CBDRx18', and selecting progeny that retain the molecular marker profile of hemp cultivar 'CBDRx18'.

Expression Vectors for Hemp Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene. Another commonly used selectable marker gene is the hygromycin phosphotransferase gene.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.*, 13:67 (1987); Shah, et al., *Science*, 233:478 (1986); Charest, et al., *Plant Cell Rep.*, 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.*, 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

Expression Vectors for Hemp Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.*, 20:49 (1992); Knox, C., et al., *Plant Mol. Biol.*, 9:3-17 (1987); Lerner, et al., *Plant Physiol.*, 91:124-129 (1989); Frontes, et al., *Plant Cell*, 3:483-496 (1991); Matsuoka, et al., *Proc. Natl. Acad. Sci.*, 88:834 (1991); Gould, et al., *J. Cell. Biol.*, 108:1657 (1989); Creissen, et al., *Plant* 2:129 (1991); Kalderon, et al., *Cell*, 39:499-509 (1984); Steifel, et al., *Plant Cell*, 2:785-793 (1990).

Foreign Protein Genes and Agronomic Genes: Transformation

With transgenic plants according to one embodiment, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.*, 114:92-6 (1981).

According to an embodiment, the transgenic plant provided for commercial production of foreign protein is a hemp plant. In another embodiment, the biomass of interest is fiber. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology*, CRC Press, Inc., Boca Raton, 269:284 (1993). Map information concerning chromosomal location is useful for proprietary protection of a subject transgenic plant.

Likewise, by means of one embodiment, plants can be genetically engineered to express various phenotypes of agronomic interest. Through the transformation of hemp, the expression of genes can be altered to enhance disease tolerance, insect tolerance, herbicide tolerance, agronomic quality, and other traits. Transformation can also be used to insert DNA sequences which control or help control male-sterility. DNA sequences native to hemps, as well as non-native DNA sequences, can be transformed into hemps and used to alter levels of native or non-native proteins. Various promoters, targeting sequences, enhancing sequences, and other DNA sequences can be inserted into the genome for the purpose of altering the expression of proteins. The interruption or suppression of the expression of a gene at the level of transcription or translation (also known as gene silencing or gene suppression) is desirable for several aspects of genetic engineering in plants.

Many techniques for gene silencing are well-known to one of skill in the art, including, but not limited to, knock-outs (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., *PNAS USA*, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., *EMBO J.*, 11:1525 (1992); Perriman, et al., *Antisense Res. Dev.*, 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular hemp cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Tissue Culture

Further reproduction of the variety can occur by tissue culture and regeneration. Tissue culture of various tissues of cannabis and regeneration of plants therefrom is well-known and widely published. Thus, another aspect or embodiment is to provide cells which upon growth and differentiation produce hemp plants having the physiological and morphological characteristics of hemp cultivar 'CBDRx18'.

Tissue culture of various tissues of Cannabis and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce Cannabis plants having the physiological and morphological characteristics of 'CBDRx18'.

Industrial Hemp

The term 'hemp', under the Agriculture Improvement Act of 2018, means the plant *Cannabis sativa* L. and any part of that plant, including the seeds thereof and all derivatives, extracts, cannabinoids, isomers, acids, salts, and salts of isomers, whether growing or not, with a delta9 tetrahydrocannabinol concentration of not more than 0.3 percent on a dry weight basis.

Industrial hemp (also known as textile hemp) has many uses. The stem of this fiber crop supplies both cellulosic and woody fibers. The core is lignified, while the cortex harbors long cellulose-rich fibers, known as bast fibers. Some of uses of industrial hemp include paper, textiles, biodegradable plastics, construction, body care products (for example, oils and lotions), food (for example flour, protein powder, coffee, milk, etc.), animal food, and fuel. Hemp pellets are produced from Cannabis woody fibers, also known as "shivs" or "hurds". The fiber is first separated and goes to make clothing and other products. The large shiv particles can then be used in construction in combination with lime. After all this processing has taken place there are small shiv particles remaining which can be processed into hemp pellets. Hemp bast fibers are used in the biocomposite sector as a substitute of glass fibers. The automotive industry is particularly keen on using hemp bast fibers to produce bioplastics; this material is stronger than polypropylene plastic and lighter in weight.

Also of use are cannabinoids, which are a group of chemical compounds derived from *Cannabis sativa*. There are at least 85 different cannabinoids that can be isolated from cannabis. Cannabinoids are cyclic molecules exhibiting particular properties, such as the ability to easily cross the blood-brain barrier, weak toxicity, and few side effects.

The most notable cannabinoids produced by cannabis are Δ9-tetrahydrocannabinol (i.e., THC) and cannabidiol (i.e., CBD).

In the cannabis plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated to produce THC. The pathway for THCA biosynthesis is similar to that which produces the bitter acid humulone in hops. See Fellermeier et al., (1998, "Prenylation of olivetolate by a hemp transferase yields cannabigerolic acid, the precursor of tetrahydrocannabinol". FEBS Letters 427 (2): 283-5); de Meijer et al. I, II, III, and IV (I: 2003, Genetics, 163:335-346; II: 2005, Euphytica, 145:189-198; III: 2009, Euphytica, 165:293-311; and IV: 2009, Euphytica, 168:95-112.)

CBD is a cannabinoid found in cannabis. Cannabidiol has displayed sedative effects in animal tests (Pickens, 1981, "Sedative activity of cannabis in relation to its delta'-trans-tetrahydrocannabinol and cannabidiol content". Br. J. Pharmacol. 72 (4): 649-56). Some research, however, indicates that CBD can increase alertness, and attenuate the memory-impairing effect of THC. (Nicholson et al., June 2004, "Effect of Delta-9-tetrahydrocannabinol and cannabidiol on nocturnal sleep and early-morning behavior in young adults" J Clin Psychopharmacol 24 (3): 305-13; Morgan et al., 2010, "Impact of cannabidiol on the acute memory and psychotomimetic effects of smoked cannabis: naturalistic study, The British Journal of Psychiatry, 197:258-290). It may decrease the rate of THC clearance from the body, perhaps by interfering with the metabolism of THC in the liver. Medically, it has been shown to relieve convulsion, inflammation, anxiety, and nausea, as well as inhibit cancer cell growth (Mechoulam, et al., 2007, "Cannabidiol—recent advances". Chemistry & Biodiversity 4 (8): 1678-1692.) Recent studies have shown cannabidiol to be as effective as atypical antipsychotics in treating schizophrenia (Zuardi et al., 2006, "Cannabidiol, a Cannabis sativa constituent, as an antipsychotic drug" Braz. J. Med. Biol. Res. 39 (4): 421-429.). Studies have also shown that it may relieve symptoms of dystonia (Consroe, 1986, "Open label evaluation of cannabidiol in dystonic movement disorders". The International journal of neuroscience 30 (4): 277-282). CBD reduces growth of aggressive human breast cancer cells in vitro and reduces their invasiveness (McAllister et al., 2007, "Cannabidiol as a novel inhibitor of Id-1 gene expression in aggressive breast cancer cells". Mol. Cancer. Ther. 6 (11): 2921-7.)

According to a 2013 review published in the British Journal of Clinical Pharmacology, studies have found CBD to possess antiemetic, anticonvulsant, antipsychotic, anti-inflammatory, anti-oxidant, anti-tumoral, anxiolytic and anti-depressant effects. CBD also possess an important antibacterial effect.

Industrial hemp has attractiveness as a source of CBD because it is available in huge amounts, as a waste product from various industries. At the same time, because of the relatively low content of cannabinoids, the use of industrial hemp poses additional challenges in making the extraction process economically viable.

Cannabinoids

Cannabinoids act on endogenous cannabinoid receptors located throughout the human body (Kreitzer and Stella, 2009, "The therapeutic potential of novel cannabinoid receptors", Pharmacology & Therapeutics 122 (2): 83-96). These receptors are present in humans because the human body manufactures a similar class of cannabinoids known as the endocannabinoids (Pertwee et al., 2010, "International Union of Basic and Clinical Pharmacology. LXXIX. Cannabinoid Receptors and Their Ligands: Beyond CB1 and CB2", Pharmacological Reviews 62 (4): 588-631).

The demand for the medicinal properties of cannabinoids derived from Cannabis is growing. Over the last 15 years, medicinal marijuana has gained similar regulatory ground as hemp. This is a reflection of consumer demand. In 2013, medical marijuana sales were estimated at 1.5 billion dollars. The medicinal effects of cannabinoids on human health continue to be validated as clinical research in this field expands and gains traction (Scott et al., 2014, "The Combination of Cannabidiol and Δ9-Tetrahydrocannabinol Enhances the Anticancer Effects of Radiation in an Orthotopic Murine Glioma Model", Molecular Cancer Therapeutics 13 (12): 2955-2967). The ability to create this medicine without THC is highly desired by many patients and regulatory agencies.

Terpenes are a large class of volatile organic hydrocarbons. In plants, they function as hormones (e.g. abscisic acid), as photosynthetic pigments (e.g. carotenoids) and are involved in many other vital physiological processes. Secondary terpenoids (secondary metabolites) account for the majority of terpenoid molecular structural diversity. The secondary terpenoids play a major role in the plant's response to environmental factors such as such as pathogen and photooxidative stresses (Tholl, 2006, "Terpene synthases and the regulation, diversity and biological roles of terpene metabolism", Current Opinion in Plant Biology 9 (3): 297-304). Apart from their functions in the plant, terpenes from hops (Humulus lupulus) such as myrcene and humulene serve as major aromatic and flavor compounds in beer. Cannabis synthesizes many terpenes including myrcene and humulene.

Cannabis normally reproduces under a dioecious system where male (staminate) and female (pistillate) flowers develop on separate plants. Monoecious plants (containing both male and female flowers) do exist. Female floral anatomy is characterized by pistils protruding from a calyx covered with resinous glandular trichomes. The glandular trichomes of the female flower are the primary site of cannabinoid synthesis. The female calyx contains ovaries and, therefore, is the site of seed development when fertilized by pollen produced by a male plant.

A vast majority of the Cannabis produced in the United States is done so by clonal propagation. Under this production scheme, meristems are cut from a selected plant and treated by various methods to induce rooting so that many, genetically identical progeny may be derived from the original. This is primarily done because breeding Cannabis seeds which consistently express a particular cannabinoid profile, often elevated for a particular cannabinoid (e.g. THC), is generally regarded as difficult. The simplicity of breeding varieties to be produced under a clonal reproduction system is quickly offset by the cost of clonal production, among other factors (Mckey et al., 2010, "The evolutionary ecology of clonally propagated domesticated plants", New Phytologist 186 (2): 318-332). There is a need in the industry for industrial hemp varieties which are reliably low in THC when produced in diverse environmental conditions and which express elevated levels of certain other cannabinoids. The present invention provides a Cannabis variety that consistently and reproducibly has nearly zero THC (thus qualifying as industrial hemp) and elevated levels of CBD.

Industrial Uses

Hemp has a wide variety of uses in the commodity area. Some of uses of industrial hemp include paper, textiles, biodegradable plastics, construction, body care products (for example, oils and lotions), food (for example flour, protein powder, coffee, milk, etc.), animal food, and fuel. Hemp pellets are produced from *Cannabis* woody fibers, also known as "shivs" or "hurds". The fiber is first separated and goes to make clothing and other products. The large shiv particles can then be used in construction in combination with lime. After all this processing has taken place there are small shiv particles remaining which can be processed into hemp pellets. Hemp bast fibers are used in the biocomposite sector as a substitute of glass fibers. The automotive industry is particularly keen on using hemp bast fibers to produce bioplastics; this material is stronger than polypropylene plastic and lighter in weight.

Also of use are cannabinoids, which are a group of chemical compounds derived from *Cannabis sativa*. There are at least 85 different cannabinoids that can be isolated from cannabis. Cannabinoids are cyclic molecules exhibiting particular properties, such as the ability to easily cross the blood-brain barrier, weak toxicity, and few side effects. The most notable cannabinoids produced by cannabis are A9-tetrahydrocannabinol (i.e., THC) and cannabidiol (i.e., CBD). Cannabinoids may be formulated as an extract, a tincture, or an oil. Cannabinoids are cyclic molecules exhibiting particular properties, such as the ability to easily cross the blood-brain barrier, weak toxicity, and few side effects. The most notable cannabinoids produced by cannabis are A9-tetrahydrocannabinol (i.e., THC) and cannabidiol (i.e., CBD).

According to a 2013 review published in the British Journal of Clinical Pharmacology, studies have found CBD to possess antiemetic, anticonvulsant, antipsychotic, anti-inflammatory, anti-oxidant, anti-tumoral, anxiolytic and anti-depressant effects. CBD also possess an important antibacterial effect.

Industrial hemp has attractiveness as a source of CBD because it is available in huge amounts, as a waste product from various industries. At the same time, because of the relatively low content of cannabinoids, the use of industrial hemp poses additional challenges in making the extraction process economically viable.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions, and sub-combinations as are within their true spirit and scope.

One embodiment may be embodied in other specific forms without departing from its spirit or essential characteristics. The described embodiments are to be considered in all respects only as illustrative and not restrictive. All changes which come within the meaning and range of equivalency of the claims are to be embraced within their scope.

Various embodiments, include components, methods, processes, systems and/or apparatus substantially as depicted and described herein, including various embodiments, sub-combinations, and subsets thereof. Those of skill in the art will understand how to make and use an embodiment(s) after understanding the present disclosure.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the embodiment(s) requires more features than are expressly recited in each claim. Rather, as the following claims reflect, inventive aspects lie in less than all features of a single foregoing disclosed embodiment. Thus, the following claims are hereby incorporated into this Detailed Description.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed.

DEPOSIT INFORMATION

A deposit of least plant tissue of the FRTJC, LLC proprietary hemp cultivar 'CBDRx18' disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Maine 04544. The date of deposit was May 29, 2024. The NCMA No. is 202405004. The deposit of plant tissue was taken from the same deposit maintained by FRTCJ, LLC since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

The invention claimed is:

1. A plant of hemp cultivar 'CBDRx18', wherein a representative sample of tissue of said hemp cultivar was deposited under NCMA No. 202405004.

2. A plant part of the plant of claim 1, wherein the plant part comprises at least one cell of hemp cultivar 'CBDRx18'.

3. A hemp plant, or a part thereof, wherein the plant has all of the physiological and morphological characteristics of the hemp cultivar 'CBDRx18' of claim 1.

4. A tissue or cell culture of regenerable cells produced from the plant of claim 1.

5. The tissue or cell culture of claim 4, comprising tissues or cells from a plant part selected from the group consisting of leaves, pollen, embryos, cotyledons, hypocotyl, meristematic cells, roots, root tips, pistils, anthers, flowers, and stems.

6. A hemp plant regenerated from the tissue or cell culture of claim 5, wherein said plant has all of the morphological and physiological characteristics of hemp cultivar 'CBDRx18'.

7. A method of vegetatively propagating the plant of claim 1, comprising the steps of:
   collecting tissue or cells capable of being propagated from said plant;
   cultivating said tissue or cells to obtain proliferated shoots; and
   rooting said proliferated shoots to obtain rooted plantlets; or
   cultivating said tissue or cells to obtain proliferated shoots, or to obtain plantlets.

8. A hemp plant produced by growing the plantlets or proliferated shoots of claim 7, wherein the plant has all of the morphological and physiological characteristics of hemp cultivar 'CBDRx18'.

9. A method for producing an embryo or seed, wherein the method comprises crossing the plant of claim 1 with another plant and harvesting the resultant embryo or seed.

10. A method of determining the genotype of the hemp plant of claim 1, wherein said method comprises obtaining a sample of nucleic acids from said plant and detecting in said nucleic acids a plurality of polymorphisms.

11. A method of producing a hemp plant tolerant to an herbicide or insecticide, or resistant to a disease, wherein the method comprises transforming the hemp plant of claim 1 with a transgene, wherein said transgene confers resistance or tolerance to said herbicide, insecticide, or disease.

12. A method for developing a hemp plant in a plant breeding program, comprising applying to a plant of hemp cultivar 'CBDRx18' plant breeding techniques, comprising crossing, recurrent selection, or mutation breeding, wherein said mutation breeding selects for a mutation that is spontaneously or naturally induced or artificially induced, backcrossing, pedigree breeding, marker enhanced selection, haploid/double haploid production, or transformation, wherein a representative sample of plant tissue of 'CBDRx18' was deposited under NCMA No. 20245004, wherein application of said techniques results in development of a hemp plant.

13. A method of introducing a mutation into the genome of hemp plant 'CBDRx18', said method comprising applying mutagenesis to of the plant, or plant part thereof, of claim 1, wherein said mutagenesis is selected from the group consisting of temperature, long-term seed storage, tissue culture conditions, ionizing radiation, chemical mutagens, or targeting induced local lesions in genomes, and wherein the resulting plant comprises at least one genome mutation.

14. A method of editing a gene in the genome of hemp plant 'CBDRx18' of claim 1, said method comprising utilizing any one of the following: zinc finger nucleases, transcription activator-like effector nucleases (TALENs), engineered homing endonucleases/meganucleases, and the clustered regularly interspaced short palindromic repeat (CRISPR)-associated protein9 (Cas9) system.

15. A hemp plant produced by the method of claim 14, wherein said plant comprises said edited gene and otherwise has all of the morphological and physiological characteristics of hemp cultivar 'CBDRx18'.

16. A method of producing a hemp plant comprising a desired trait, the method comprising introducing a transgene conferring the trait into the plant of claim 1.

17. A hemp plant produced by the method of claim 16, wherein said plant has the desired trait and otherwise has all of the morphological and physiological characteristics of hemp cultivar 'CBDRx18'.

* * * * *